United States Patent [19]

Young et al.

[11] Patent Number: 5,180,475
[45] Date of Patent: Jan. 19, 1993

[54] SYSTEM AND METHOD FOR CONTROLLING ELECTROOSMOTIC FLOW

[75] Inventors: James E. Young, La Honda; Douglass McManigill; Jurgen A. Lux, both of Palo Alto, all of Calif.

[73] Assignee: Hewlett-Packard Company, Palo Alto, Calif.

[21] Appl. No.: 754,797

[22] Filed: Sep. 4, 1991

[51] Int. Cl.$^5$ .............................................. G01N 27/26
[52] U.S. Cl. .............................. 204/180.1; 204/299 R
[58] Field of Search ........................... 204/299 R, 180.1

[56] References Cited

U.S. PATENT DOCUMENTS

| | | | |
|---|---|---|---|
| 3,563,872 | 2/1971 | Huebner | 204/180 |
| 3,915,827 | 10/1975 | Davies | 204/180 G |
| 4,394,246 | 7/1983 | Richman et al. | 204/301 |
| 4,690,749 | 9/1987 | Van Alstine et al. | 204/299 R |
| 4,705,616 | 11/1987 | Andresen et al. | 204/299 R |
| 4,842,701 | 6/1989 | Smith et al. | 204/180.1 |
| 4,931,328 | 6/1990 | Swedberg | 428/36.91 |
| 4,936,974 | 6/1990 | Rose et al. | 204/299 R |

FOREIGN PATENT DOCUMENTS 3-172756  7/1991  Japan .

Primary Examiner—John Niebling
Assistant Examiner—David G. Ryser

[57] ABSTRACT

A system and method for controlling the rate of electroosmotic flow in capillary electrophoresis. A first high voltage power supply is electrically connected to the inlet end of a capillary tube, while a second high voltage power supply is connected at an outlet end. The potential difference across the capillary tube is therefore the difference between the high voltages. Electroosmotic flow can be controlled by varying the two high voltages correspondingly to maintain the same potential difference but to achieve a different voltage offset relative to ground. Optionally, the voltage offset may be varied during electrophoresis analysis to slow migration during periods in which constituents are closely spaced and to speed migration when constituents are sufficiently spaced apart. A conductive capillary tube coating which is preferably grounded defines an external control area for electroosmotic flow. A detector is located downstream of the external control area, so that the coating is a unitary layer.

15 Claims, 4 Drawing Sheets

SYSTEM AND METHOD FOR CONTROLLING ELECTROOSMOTIC FLOW

DESCRIPTION

Technical Field

The present invention relates generally to electrophoretic processes and more particularly to controlling electroosmotic flow in capillary electrophoresis.

Background Art

Applications for electrophoresis, an analytical technique for separating and identifying constituents in a sample, include the determination of a sample's purity, the determination of molecular weights for proteins and nucleic acids, the mapping of nucleic acid primary structures, i.e. DNA and RNA sequence analyses, and the definition of phenotypic variance of a protein at the molecular level. Electrophoretic techniques rely on the fact that each molecular species has a unique combination of mass, size, shape, charge, density and sub-unit structure, all of which result in mobility differences responsive to an electric field. Various electrophoretic techniques use one or more of these properties to cause varying degrees of molecular separation via the migration of molecular species under an electric field.

Capillary electrophoresis is a technique using a capillary tube which is filled with a conductive fluid, as for example a buffer solution. A small amount of sample is introduced at one end of the capillary tube, whereafter a high potential difference is applied across the ends of the tube. Electroosmotic flow and differences in electrophoretic mobilities combine to provide a spatial separation of constituents of the sample solution at the outlet end of the capillary tube.

Electroosmotic flow is the movement of a liquid relative to a stationary charge surface as a result of an electric field applied to the liquid. U.S. Pat. No. 4,936,974 to Rose et al. explains electroosmotic flow as a result of charge accumulation at the capillary surface due to preferential adsorption of anions from the buffer solution that fills the bore of the capillary tube. The negative charge of the anions attracts a thin layer of mobile positively charged buffer ions, which accumulate adjacent to the inner surface. The longitudinally extending electric field that is applied across the capillary tube attracts the positive ions which are hydrated by water toward a grounded outlet end of the capillary tube, viscously dragging other hydrated molecules. This dragging of molecules applies to neutral and negatively charged molecules, as well as positively charged molecules. The result is a bulk flow of the sample in the buffer solution toward the grounded outlet end of the capillary tube. Consequently, electroosmotic flow provides a means for moving neutral and negatively charged constituents of a sample toward a ground electrode.

Electrophoretic migration is the movement of charged constituents in response to an electric field. A positively charged molecule will be accelerated through the electroosmotic flow toward the ground electrode. Negatively charged molecules may be repelled by the ground electrode, but the force of the electroosmotic flow overcomes the repulsion and advances the negatively charged molecules.

As a result, for an analysis in which a positive electrode is applied to the inlet end of the capillary tube and a ground electrode is applied to the outlet end, a spatial separation will occur with positively charged constituents exiting first, followed by neutral constituents and then negatively charged constituents. Each constituent of a sample may be identified by detecting the time required for the constituent to travel through the capillary tube. The quantity of the constituent within the sample is determined by the height and/or area of a signal trace on an electropherogram during a period of detection of that constituent. Ultraviolet detectors placed proximate to the outlet end of the capillary tube are commonly used, but other detectors are known.

Obtaining an accurate analysis requires that each sample constituent be moved to the detection area. Often, the sample is introduced into the inlet end of the capillary tube by insertion of the inlet end into a sample vial, whereafter the inlet end is inserted into a first buffer vial electrically connected to the high voltage electrode. The outlet end of the capillary tube is inserted into a buffer reservoir vial connected to the ground electrode. Upon initiating the separation procedure, a negatively charged molecule may be drawn into the first buffer vial before electroosmotic flow can take full effect. Thus, these molecules will not be detected, rendering the analysis less accurate. Another problem in obtaining an accurate analysis involves resolution of constituent detections. If a sample contains a number of constituents having similar electrophoretic mobilities, an analysis may be susceptible to errors in identifying and in quantifying the constituents. Yet another problem involves external factors, such as atmospheric conditions, that may have an effect on the electrophoretic separation.

It is an object of the present invention to provide a system and a method for increasing the effectiveness and reliability of electrophoretic separation and analysis. Another object is to provide such a system and method which may be used to reduce the setup time for analysis, as well as the migration time required for the analysis.

SUMMARY OF THE INVENTION

The above objects have been met by a system and method which, instead of influencing electrophoretic separation of sample constituents by factors directly related to the electrophoretic mobilities of the sample constituents, control the rate of electroosmotic flow. By controlling electroosmotic flow and by removing influences on electroosmotic flow, the analytical procedure is improved.

The system includes a continuous flow electrophoresis apparatus having a separation capillary. The separation capillary, typically a capillary tube, has an inlet end to receive a sample and a buffer solution and has an outlet end. A first adjustable power supply is electrically connected to the inlet end, while a second adjustable power supply is connected to the outlet end. Thus, the potential difference across the capillary tube is the difference between the voltages applied by the first and second power supplies. The potential gradient is then the potential difference divided by the length of the capillary tube between the connections of the capillary tube to the first and second power supplies. In a second embodiment, the second power supply is replaced by a resistive circuit electrically connected in parallel with the capillary tube.

A voltage offset relative to ground is used to control electroosmotic flow generated within the capillary tube. That is, while the potential difference and the resulting potential gradient remain constant, the first and second power supplies are adjusted correspondingly to increase or decrease the rate of electroosmotic flow toward the outlet end of the capillary tube. In a system in which the outlet end is at a lower potential relative to ground, an increase in the voltage offset relative to ground will increase the rate of electroosmotic flow, while a decrease in the voltage offset will decrease the rate of flow.

An advantage of the present invention is that the first and second high voltage power supplies may be adjusted to best suit a particular analysis. For example, if a sample has a number of constituents with similar electrophoretic mobilities, a voltage offset that ensures a slow constituent migration past a detector may be established to enhance resolution. On the other hand, the electroosmotic flow may be increased in order to provide a speedy analysis if the electrophoretic mobilities of the various sample constituents vary by sufficient amounts.

Another advantage is that the rate of electroosmotic flow may be varied during the separation procedure. The rate of flow may be increased during analysis of separated constituents having significantly different electrophoretic mobilities and may be decreased during analysis of separated constituents having similar electrophoretic mobilities. This is especially useful in an analysis of a sample having known constituents which are to be quantified.

In a preferred embodiment, the capillary tube has a coating of electrically conductive material on an outside wall of the capillary tube. As noted above, the electroosmotic flow is a result of ionic charge on the walls of the capillary tube. A conductive coating on the exterior of the capillary tube reduces the likelihood of creation of an undesired voltage gradient along the outside wall. A homogeneous field along the outside wall prevents external forces from affecting the ionic charge. An advantage is that the electrophoretic procedure is thereby more reliable. Preferably, the electrically conductive coating is placed at ground potential. This provides a defined reference point to the voltage offset created within the capillary tube. Grounding of the conductive coating can increase the surface zeta potential. Since zeta potential affects electroosmotic flow, increasing the zeta potential will increase the rate of flow for a given voltage offset and a given potential gradient.

Whether the conductive coating is allowed to float or is grounded, the coating reduces the likelihood of electrostatic charges at the outside of the capillary tube. Because of the thinness of a capillary tube, the capillary tube is susceptible to vibrations from electrostatic effects. The elimination of the electrostatic effects by use of the conductive coating provides an undisturbed ultraviolet detection of constituent migration through the capillary tube.

The conductive coating provides an external control area of the capillary tube. A difficulty associated with an external control area involves the optical coupling of a detector to the capillary tube. One solution is to form a window through the coating and to provide a conductive bridge across the coating. The present invention, however, utilizes a unitary external control area and places the detector downstream of that area. Thus, the detector which is coupled to the capillary tube to detect constituent separation while the constituents remain within a capillary tube does not affect electroosmotic flow.

BEST MODE FOR CARRYING OUT THE INVENTION

Figure 1:
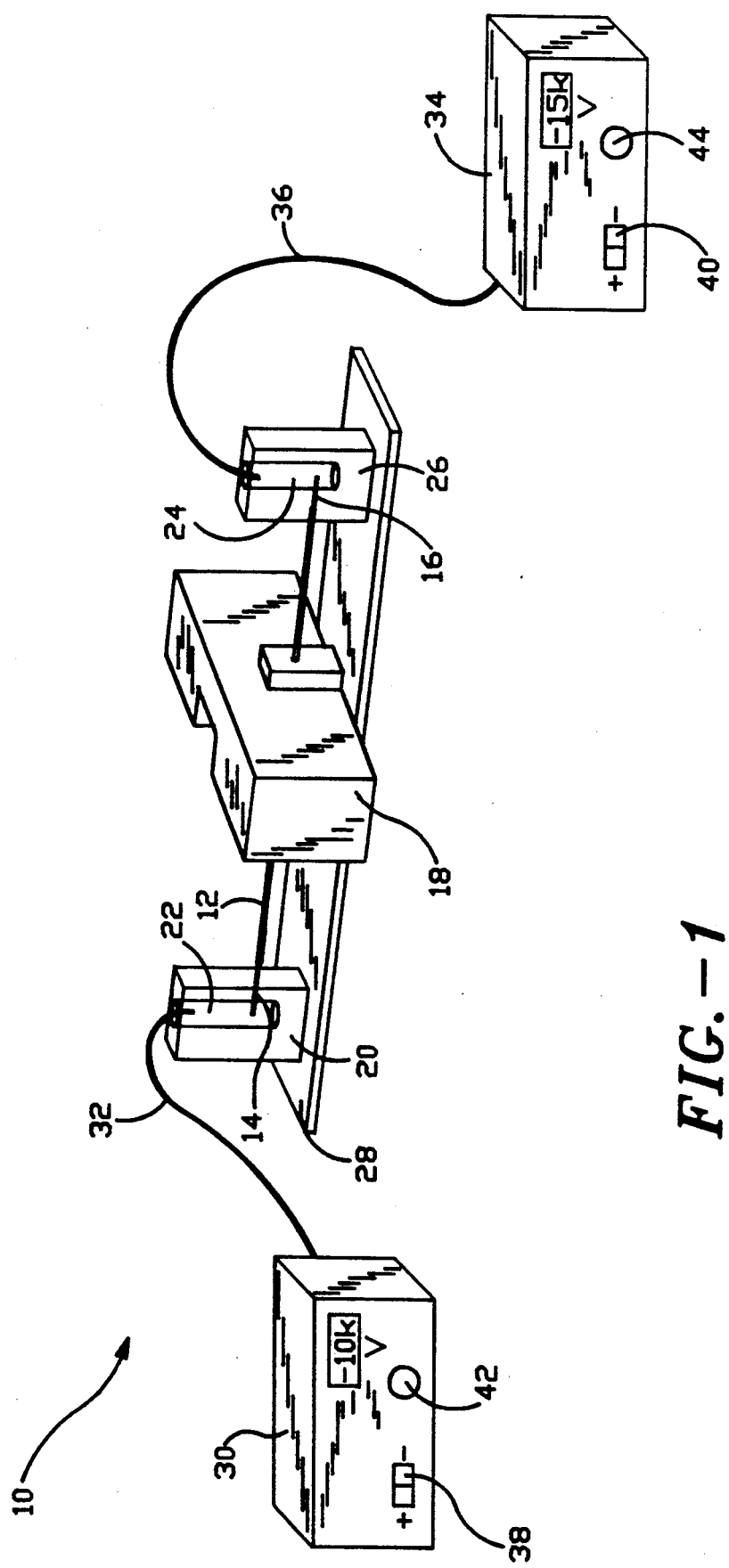
FIG. 1 is a schematic view of a continuous flow electrophoresis system for controlling the rate of electroosmotic flow.

With reference to FIG. 1, an electrophoretic system 10 is shown as including a capillary tube 12 having an inlet end 14 and an outlet end 16. The capillary tube is of the type known in the art. A fused silica tube having a coating of polyimide may be used. Such a capillary tube is flexible but has a material memory that urges the tube to return into a generally straight condition after flexing. The capillary tube has an inside diameter of 50 microns and an outside diameter that is typically in the range of 140 microns to 360 microns, but these dimensions are not critical.

A detector 18 is located along the length of the capillary tube 12. The polyimide coating is removed from the capillary tube at the optical coupling of the tube to the detector. In capillary zone electrophoresis, ultraviolet absorbance detectors are commonly used, but other detectors are known. For example, detection may also occur using a chemi-luminescence, refractive index, or conductivity detector. The optical coupling of the detector to the capillary tube permits detection of movement within the capillary tube.

The inlet end 14 of the capillary tube 12 is inserted into a container 20 having a sample vial 22. At the opposite side of the detector 18 is a buffer reservoir vial 24 that is in fluid communication with the outlet end 16 of the capillary tube. The buffer reservoir vial is housed within a container 26. The two containers 20 and 26 and the detector 18 rest on a table 28.

A first high voltage power supply 30 is electrically connected to the supply vial 22 via a power line 32 that represents an anode electrode. The first power supply 30 provides a high voltage, shown in FIG. 1 as −10 k volts, at the supply vial 22. However, this high voltage is not the potential difference across the capillary tube 12. The potential difference is determined by the voltage at the buffer reservoir vial 24. This voltage is provided by a second high voltage power supply 34 in electrical communication with the buffer reservoir vial 24 via a power line 36 that represents the cathode electrode. The second power supply 34 is illustrated as being set to provide a second high voltage of −15 k volts. Thus, the potential difference across the capillary tube 12 is 5 k volts. A standard potential gradient in capillary zone electrophoresis is 200 v/cm. To achieve this standard, the length of the capillary tube 12 would then be 25 cm.

Each of the high voltage power supplies 30 and 34 is a bipolar device having a polarity-select switch 38 and 40 to adjust the polarity of the associated electrode 32 and 36. Voltage-adjustment dials 42 and 44 allow a user to accurately set the outputs of the power supplies.

Figure 2:
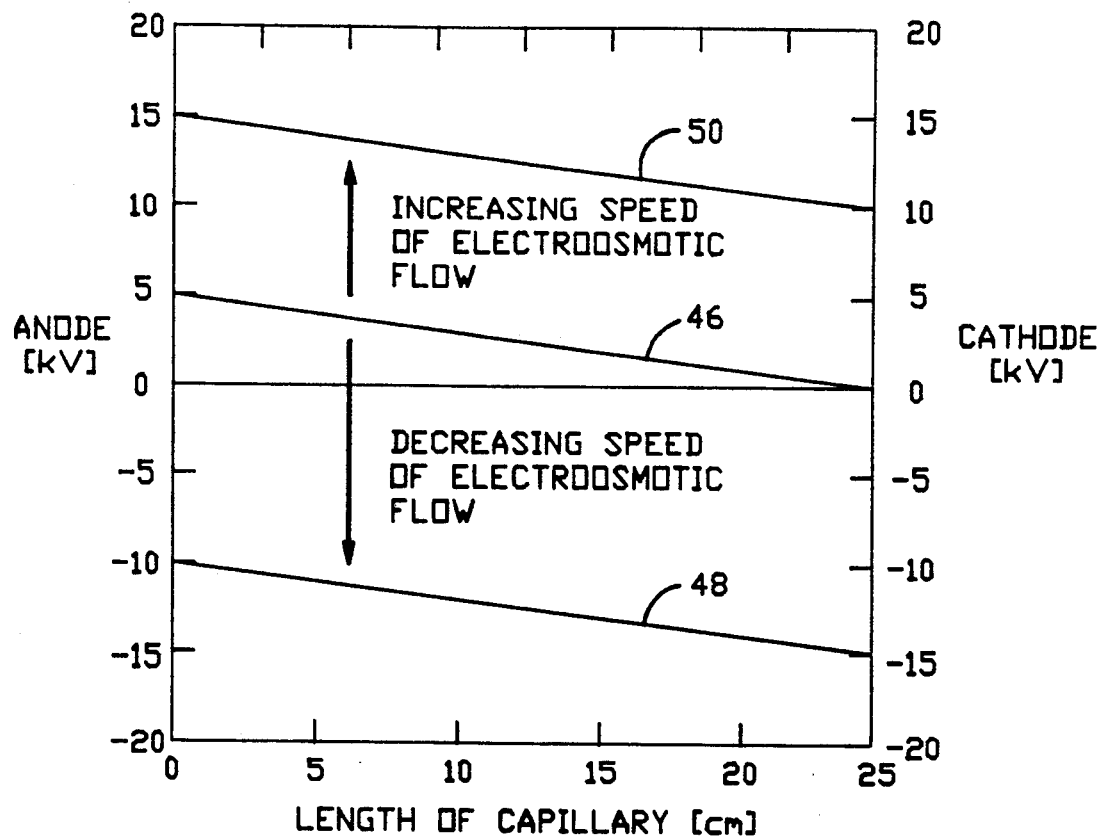
FIG. 2 is a graph showing the effects of varying the voltage offset of the system of FIG. 1.

In the prior art, the potential difference of 5 k volts would commonly have been achieved by setting the anode electrode 32 at 5 k volts and the cathode electrode 36 at ground potential. For a given sample in such a system, the direct effect on sample constituents Would be the same as the system shown in FIG. 1. However, by using the first and second power supplies 30 and 34, the present invention provides a voltage offset relative to ground. This voltage offset and its effects are shown graphically in FIGS. 2 and 3. The conventional prior art voltage configuration is shown by line 46 as having an anode electrode 32 at 5 kv and a cathode electrode at 0 v. Line 48 illustrates the voltage gradient established by the configuration of FIG. 1. A third line 50 may be obtained by adjusting the polarities and the voltage outputs of the two power supplies. The voltage offset of the lines relative to ground affects the rate of electroosmotic flow within the capillary tube. That is, a change in the voltage offset changes the electroosmotic flow.

Figure 3:
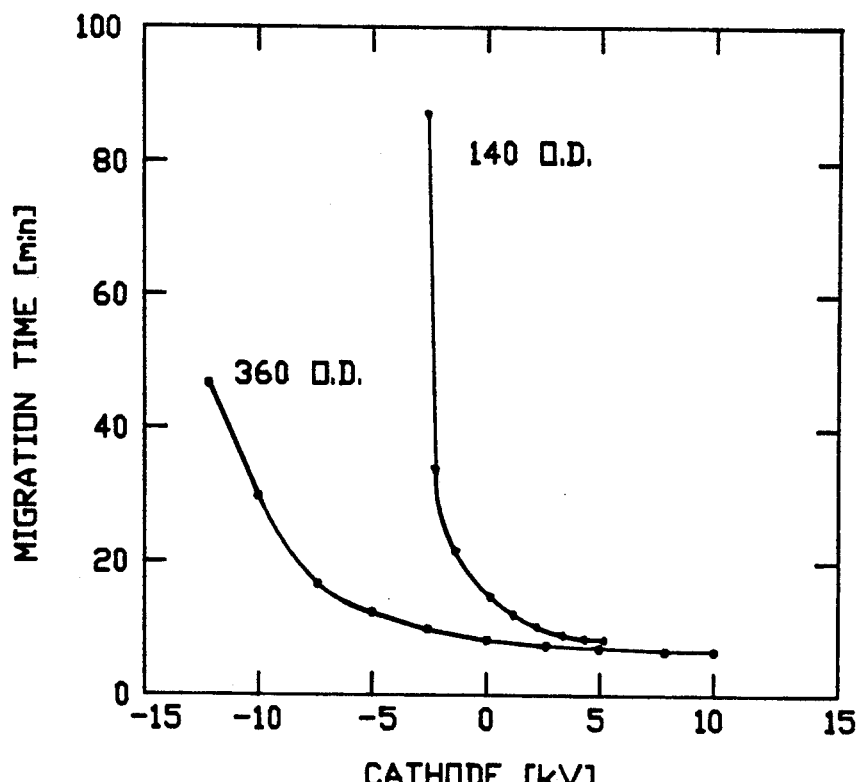
FIG. 3 is a graph of the time of analysis required for electrophoretic migration with changes in voltage offset.

The graph of FIG. 3 illustrates the relationship between the voltage offset and the time required for analysis. Using a capillary tube having an outside diameter of 140 microns, the migration time is approximately 17 minutes if the cathode electrode is set at ground and the anode electrode applies a voltage of 5 k volts. In comparison, the voltage configuration of FIG. 1, in which the respective voltages are $-15$ k volts and $-10$ k volts, slows the analysis to one that requires more than 80 minutes. The reduction in speed is a direct result of a decrease in the rate of electroosmotic flow. Such a decrease would be beneficial where a sample to be analyzed includes a number of constituents having similar electrophoretic mobilities, since the resolution would be enhanced by the reduction in flow rate. In comparison, providing a positive voltage offset increases the rate of electroosmotic flow to provide a faster analysis for samples having constituents with electrophoretic mobilities which are sufficiently different that resolution is not a major concern. The effects of increasing the voltage at the cathode electrode while maintaining a potential difference of 5 k volts decrease as the voltage offset moves positively, but the effects are significant.

Also shown in FIG. 3 is a graphing of the results of similar adjustments of the high voltage offset in use with a capillary tube having an outside diameter of 360 microns. The curve is smoother than the graphing of the changes in migration time through the smaller capillary tube. This is at least partially explained by the use of a capillary tube having a grounded outside coating during the result plotting of FIG. 3. The grounded outside coating has less effect on a capillary tube having a thicker inside coating or coatings of dielectric material. The grounding of a capillary coating will be described more fully below.

Figure 4:
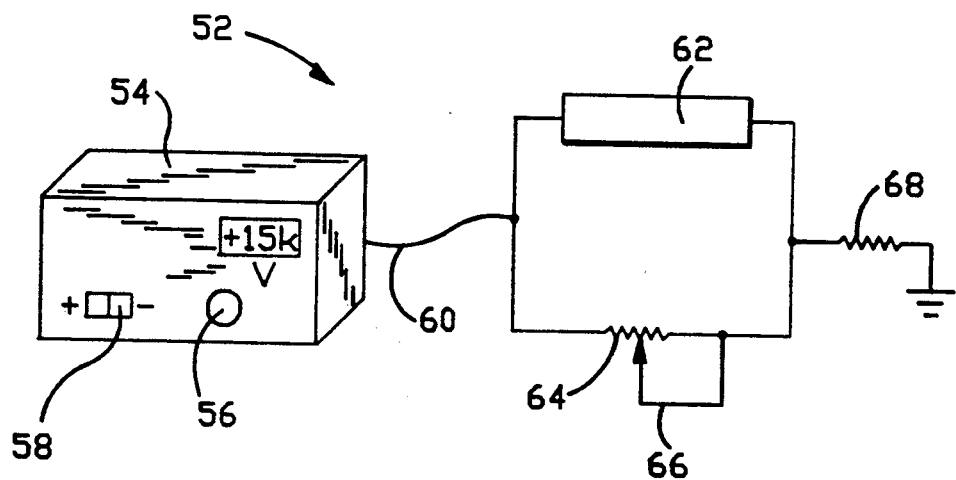
FIG. 4 is a second embodiment of an electrophoresis system for controlling the rate of electroosmotic flow.

Referring now to FIG. 4, a second embodiment of an electrophoretic system 52 is shown schematically as including a single bipolar high voltage power supply 54. The high voltage power supply has an adjustment dial 56 and a polarity-select switch 58. The output line 60 of the power supply is connected to the anode end of a capillary tube 62 and to a potentiometer 64. A center tap 66 of the potentiometer and a cathode end of the capillary tube are electrically linked. A resistor 68 provides a ground connection for the center tap and the cathode end. Thus, the voltage offset relatively to ground can be established by setting the desired anode voltage from the power supply 54, and then adjusting the potentiometer 64 to achieve the desired cathode voltage. Optionally, the potentiometer can be replaced with a resistor ladder, so that the resistance adjustment is precisely stepped. Moreover, the electrical connection between a single high voltage power supply and opposite ends of a capillary tube so as to provide first and second high voltages may be accomplished in other manners.

Figure 6:
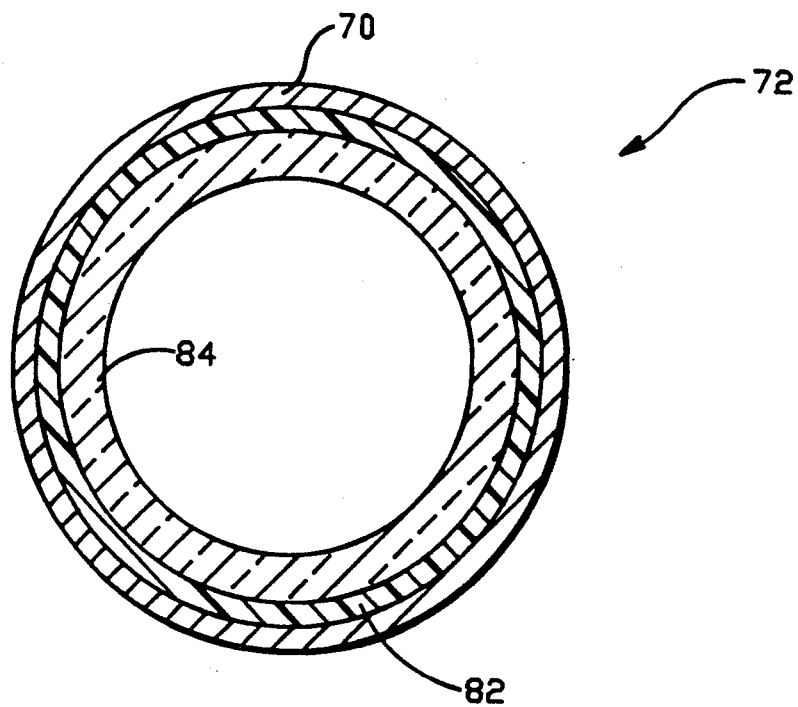
FIG. 6 is a side sectional view of the capillary tube of FIG. 5.
Figure 5:
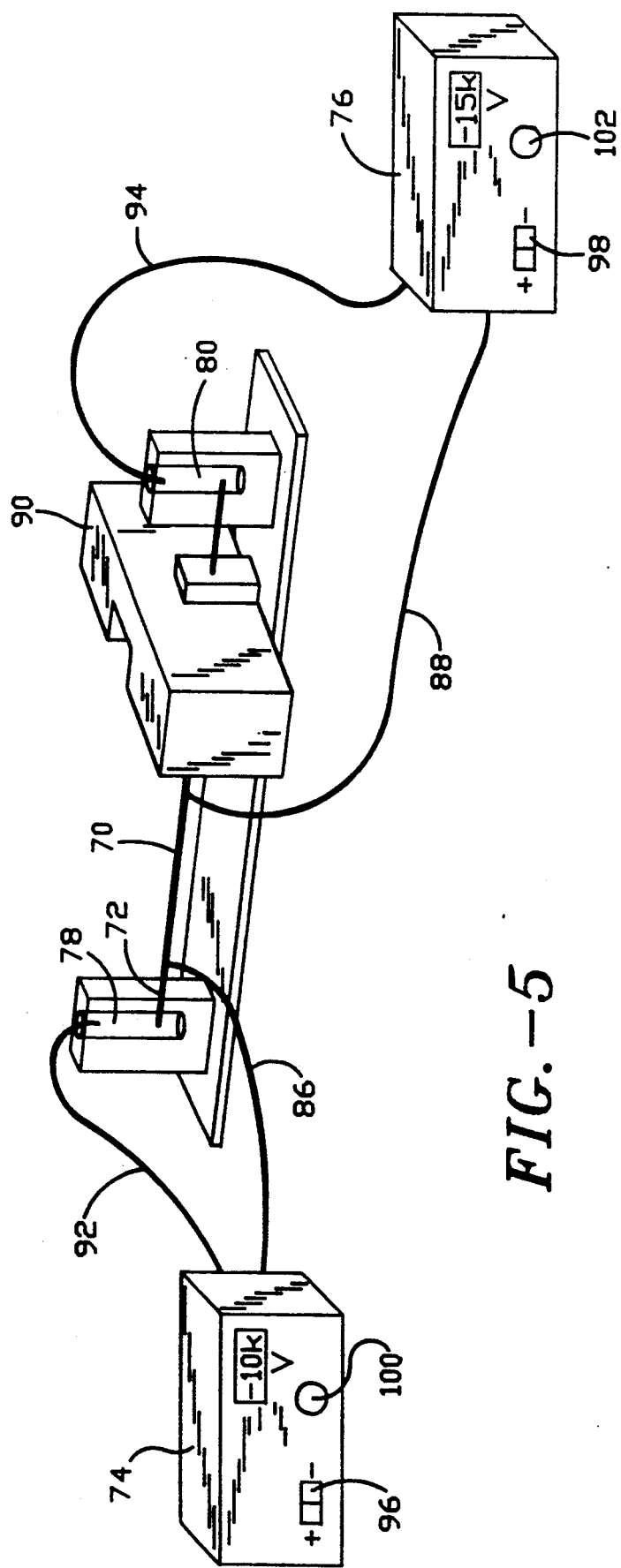
FIG. 5 is a schematic view of an electrophoresis system having an external control area and a detector placed outside the control area.

Referring now to FIGS. 5 and 6, electroosmotic flow can be further controlled by providing a conductive coating 70 on the outside wall of a capillary tube 72. Again, first and second high voltage power supplies 74 and 76 are shown connected to a supply vial 78 and a buffer reservoir vial 80 by power lines 92 and 94, respectively. The power supplies include polarity-select switches 96 and 98 and voltage-adjustment dials 100 and 102. The vials are in fluid communication with opposite ends of the capillary tube 72.

The conductive coating 70 on the capillary tube 72 may be allowed to float relative to ground. The conductive coating decreases the likelihood of an electrostatic field developing about the exterior of the capillary tube. Such a field would reduce the reliability of an electrophoretic analysis. Electroosmotic flow is a result of an electrical double layer of ions forming at the capillary interior as an electric field is imposed across the capillary tube. Consequently, any charge at the exterior of the tube has the potential of adversely affecting ion collection on the inside surface. The conductive coating 70 reduces the likelihood of a voltage gradient being created along the exterior wall of the capillary tube 72.

By "conductive coating" what is meant is a coating that may be used to establish or to eliminate an electrical field along the capillary tube, wherein the means of establishing or eliminating the electric field is by electrical conduction. The conductive coating 70 of the capillary tube 72 may be a nickel print on a standard polyimide layer 82 of a fused silica capillary layer 84. Deposition techniques known in the art may be employed. The thickness of the conductive coating 70 is not critical. Likewise, materials other than nickel, such as aluminum and conductive polymers, may be utilized.

In a preferred embodiment, the conductive coating 70 is grounded, as shown by ground lines 86 and 88 of FIG. 5. In addition to creating a reference point to the voltage offset of the tube 72, the grounding of the conductive coating potentially increases the surface zeta potential. Since zeta potential affects electroosmotic flow, increasing the zeta potential increases the rate of flow. As noted above and as shown graphically in FIG. 3, a grounded outside coating has less effect as the distance between the outside coating and inside diameter of the tube 72 is increased.

Returning to FIG. 5, the conductive coating 70 defines an external control area of the capillary tube 72. External control areas in capillary zone electrophoresis typically require users to form a window through the control area in the same manner that a window is formed through polyimide in a standard capillary tube 72. However, in FIG. 5 a detector 90 is placed downstream of the external control area. Preferably, the detector 90 is located within the final four centimeters of the capillary tube. The conductive coating 70 should be terminated at approximately two centimeters from the sample vial 78 to prevent an electrical short circuit to the vial. However, the optimal distance between the conductive coating and the sample vial will vary with the voltage applied to the sample vial. At the detector end, the termination depends upon the type and size of the detector. In use with an ultraviolet detector, if the mechanism can be narrowed to five millimeters in diameter, the termination of the coating would be the two centimeters needed to prevent shorting to the buffer reservoir vial 80, plus the additional 5 millimeters. Because the detector 90 is typically grounded, shorting between the grounded conductive coating 70 and the detector is not a concern.

Whether the conductive coating is allowed to float relative to ground or is grounded as shown in FIG. 5, the conductive coating 70 reduces the likelihood of electrostatic buildup at the outside of the capillary tube 72. Electrostatic buildup can cause vibrations of the capillary tube. By eliminating the electrostatic effects, the conductive coating can provide an undisturbed ultraviolet detection of migration through the capillary tube.

While perhaps the present invention adapts most easily to use in capillary zone electrophoresis, the invention may be used with other electrophoretic separation techniques, such as capillary isoelectric focussing which separates sample constituents by isoelectric point in a pH gradient formed over the length of a capillary. After the separation has been completed, electroosmotic flow may be employed in progressing the separated constituents past a detection device, with the electroosmotic flow being controlled by use of the present invention. This applies equally to isotachophoresis, which separates sample constituents by mobilities, and to micellar electrokinetic capillary chromatography, a form of chromatography which uses a "stationary" phase that is subject to electroosmotic flow.

Moreover, while the separation capillary has been illustrated as a single capillary tube, the separation capillary may include more than one capillary column and/or may have more than one inlet, as in the above-cited U.S. Pat. No. 4,936,974 to Rose et al.

We claim:

1. A method of controlling the rate of electroosmotic flow of a sample solution comprising,
   providing an electrophoresis apparatus having a flow region,
   inducing an electroosmotic flow of a solution within said flow region,
   electrophoretically separating constituents of said solution, including applying a first voltage level to a first end of said flow region and applying a second voltage level to a second end of said flow region,
   changing the rate of electroosmotic flow along said flow region during said step of electrophoretically separating constituents by adjusting the voltage levels at each of said first and second ends relative to ground, thereby providing a third voltage level to said first end and providing a fourth voltage level to said second end, the potential difference between said first and second voltage levels being substantially equal to the potential difference between said third and fourth voltage levels, and
   continuing said step of electrophoretically separating said constituents at said changed rate of electroosmotic flow.

2. The method of claim 1 wherein said step of providing an electrophoresis apparatus is a step of providing an apparatus having a capillary tube defining said flow region.

3. The method of claim 2 wherein said capillary tube has an inner layer defining an inside diameter and has at least one outer layer, said method further comprising forming an outer layer by coating an area of said capillary tube with a conductive material, said step of forming an outer layer including leaving said first and second ends of said capillary tube free of said conductive coating.

4. The method of claim 3 further comprising electrically grounding said conductive material during said step of electrophoretically separating constituents.

5. The method of claim 3 further comprising detecting spatial separation of said constituents during migration through said capillary tube, said detecting being downstream of said coating and between said first and second ends of said capillary tube.

6. A capillary electrophoresis system comprising,
   a capillary tube having a longitudinal axial bore and an outer wall, said capillary tube having an inlet end for introducing a sample solution into said longitudinal axial bore and having an outlet end,
   supply means for applying a potential gradient along said longitudinal axial bore of said capillary tube to introduce electrophoretic migration of constituents of sample solution, said supply means generating an axially-directed electrical field along said capillary tube and a radially-directed electrical field perpendicular to said longitudinal axial bore, and
   an external control means for affecting the magnitude of said radially-directed electrical field, thereby influencing a surface zeta potential of said capillary tube, said external control means including an electrical conductive coating on a portion of said capillary tube spaced apart from said inlet and outlet ends to leave said inlet and outlet ends free of said conductive coating, said external control means further including an electrical connection of said conductive coating to ground potential.

7. The system of claim wherein said conductive coating has a terminus spaced apart from said outlet end by a distance less than 4 cm.

8. The system of claim 6 wherein said means for applying a potential gradient includes a first high voltage power supply in electrical communication with said inlet end and a second high voltage power supply in electrical communication with said outlet end.

9. The system of claim 6 wherein said conductive coating is a nickel print.

10. The system of claim 6 wherein said capillary tube is a fused silica tube having a nonconductive coating, the outer diameter of said nonconductive coating defining said outer wall of said capillary tube.

11. The system of claim 10 wherein said nonconductive coating is removed at said detection means.

12. An improved electrophoresis system in which electroosmotic flow of a solution and differences in electrophoretic mobilities of solution constituents combine to create spatial separation of said solution constituents along a capillary tube having an inlet end deposited in a first liquid reservoir and having an outlet end deposited in a second liquid reservoir, wherein the improvement comprises,
   adjustable means for applying a first high voltage to said first liquid reservoir and applying a second high voltage to said second liquid reservoir for selectively varying the rate of said electroosmotic flow of said solution within said capillary tube, wherein each of said first and second high voltages are selected to provide a desired spatial separation of said solution constituents within said capillary tube.

13. A method of controlling the rate of electroosmotic flow of a sample solution comprising, providing a capillary tube having first and second ends and having an inner layer defining an inside diameter for the flow of a sample solution there along, said capillary tube having at least one outer layer including a conductive coating along a region of said capillary tube spaced apart from said first and second ends, electrically connecting a first high voltage supply to said first end, electrically connecting a second high voltage supply to said second end, electrically grounding said conductive coating on said capillary tube, selecting a desired axial potential gradient between said first and second ends of said capillary tube, selecting a potential difference between said first and second high voltage supplies to achieve said desired axial potential gradient, selecting magnitudes, relative to ground, of voltages for said first and second high voltage supplies to achieve said potential difference and to generate a desired radially-directed electrical field for spatial separation of constituents in a sample solution, said selecting of magnitudes being a selecting of voltages less than or greater than ground, applying said selected magnitudes of voltages to said first and second ends, and detecting said separation of constituents prior to exit of said constituents from said capillary tube.

14. The method of claim 13 further comprising adjusting both of said first and second high voltage supplies during said step of detecting said separation, including selecting adjusted magnitudes of voltages to provide a second rate of separation different from the rate of separation prior to said step of adjusting both of said first and second high voltage supplies.

15. The method of claim 14 wherein said step of adjusting both of said first and second high voltage supplies is a step of providing a corresponding adjustment, thereby maintaining said desired axial potential gradient.

* * * * *

UNITED STATES PATENT AND TRADEMARK OFFICE
CERTIFICATE OF CORRECTION

PATENT NO. : 5,180,475

DATED : Jan. 19, 1993

INVENTOR(S) : James E. Young, Douglass McManigill, Jurgen A. Lux

It is certified that error appears in the above-identified patent and that said Letters Patent is hereby corrected as shown below:

Column 5, Line 10, change "Would" to --would--;

Column 8, Line 37, change "electrical" to --electrically--;

Column 8, line 43, change "claim wherein" to --claim 6 wherein--.

Signed and Sealed this

Twenty-third Day of August, 1994

Attest:

BRUCE LEHMAN

Attesting Officer

Commissioner of Patents and Trademarks